United States Patent [19]
Folkers et al.

[11] Patent Number: 4,721,775
[45] Date of Patent: Jan. 26, 1988

[54] EFFECTIVE PEPTIDES RELATED TO THE LUTEINIZING HORMONE RELEASING HORMONE FROM L-AMINO ACIDS

[75] Inventors: Karl Folkers, Austin, Tex.; Cyril Y. Bowers, New Orleans, La.; Pui-Fun L. Tang; Minoru Kubota, both of Austin, Tex.

[73] Assignee: Board of Regents, The University of Texas System, Austin, Tex.

[21] Appl. No.: 771,546

[22] Filed: Aug. 26, 1985

[51] Int. Cl.$^4$ .................................................. C07K 7/20
[52] U.S. Cl. .................................................. 530/313
[58] Field of Search .................. 530/313, 329, 330

[56] References Cited
PUBLICATIONS

Chem. Abstr., vol. 104 (1986), 32119c.
Chem. Abstr., vol. 102, (1985), 218763.
Chem. Abstr., vol. 98 (1983), 195266.
Chem. Abstr., vol. 103 (1985), 20111k.
Chem. Abstr., vol. 103 (1985), 120348.
Folkers et al., "The Follicle Stimulating Hormone", Chapter 13, *Reproductive Physiology.*
Igarashi et al., "A Hypothalamic Follicle Stimulating Hormone-Releasing Factor", Mar. 1964.
Shally et al. (1971), *B.B.R.C.,* 43: 393–399.
Matsuo et al. (1971), *B.B.R.C.,* 43: 1334–1339.
Yanaihara et al. (1972), *B.B.R.C.,* 49: 1280–1291.
Johansson et al. (1973), *B.B.R.C.,* 50: 8–13.
Currie et al. (1973), *B.B.R.C.,* 50: 14–19.
Bowers (1973), *B.B.R.C.,* 50: 20–26.
Koch et al. (1973), *B.B.R.C.,* 50: 623–629.
Coy et al. (1973), *J. Med. Chem.,* 16: 83–84.
Ling et al. (1975), *B.B.R.C.,* 63: 801–806.
Fawcett et al. (1975), *Endo.,* 96: 1311–1314.
Yu et al. (1978), *Life Sciences,* 22: 269–282.
Heber et al. (1978), *J. Physio.,* pp. 227–230.
Wise et al. (1979), *Endo.,* 104: 940–947.
Yu et al. (1979), *Neuroendo.,* 29: 54–65.
Blask et al. (1979), *Neuroendo,* 28: 36–43.
Fuchs et al. (1979), *B.B.R.C.,* 88: 92–96.
Conne et al. (1979), *B.B.R.C.,* 90: 1249–1256.
King et al. (1979), *Science,* 206: 67–69.
Sherwood et al. (1983), *P.N.A.S.,* 80: 2794–2798.
Miyamoto et al. (1984), *P.N.A.S.,* 81: 3874–3878.
Folkers et al. (1984), *B.B.R.C.,* 123: 1221–1226.

*Primary Examiner*—Delbert R. Phillips
*Attorney, Agent, or Firm*—Arnold, White & Durkee

[57] ABSTRACT

The chemical structure of the luteinizing hormone releasing hormone (LHRH) was elucidatd in 1971. Since then, a very large number of international investigators synthesized more than 100 monosubstituted and about 14 disubstituted analogs of LHRH. All of these analogs were synthesized from natural amino acids having the L-configuration. Not one of these approximately 114 analogs showed agonist activity equivalent to that of LHRH. Two of the 114 were about 60% as active, and neither one has had any utility. We have investigated the six individual L-amino acids which occur in positions 5, 7, and 8 of the four naturally occurring LHRH's which exist in porcine/ovine, salmon, and chicken tissue. There are a total of 16 peptides with these structural features, and we have discovered that not only one but five of these peptides are not only equivalent in certain assays in activity to LHRH, but that two of the five are surprisingly superior to LHRH in activity, and that two of the five have a unique and unpredictable dissociation of activity for the release of luteinizing hormone (LH) and follicle stimulating hormone (FSH). These five peptides are:

A. p-Glu His Trp Ser His Gly Leu Arg Pro Gly-NH$_2$,
B. p-Glu His Trp Ser His Gly Trp Arg Pro Gly-NH$_2$,
C. p-Glu His Trp Ser His Gly Trp Gln Pro Gly-NH$_2$,
D. p-Glu His Trp Ser His Gly Trp Leu Pro Gly-NH$_2$,
E. p-Glu His Trp Ser Tyr Gly Trp Arg Pro Gly-NH$_2$,

Peptide C might be the naturally occurring as FSHRH, because of its dissociated release of LH and FSH. The discovery for the first time of decapeptides with L-amino acids equal to or more potent than LHRH was based on about 14 years of background. Our new peptides are particularly useful in medical fields for pituitary stimulation and inhibition, for enhancement or inhibition of fertility in humans and animals, for the therapy of hormone-dependent tumors, for special effects on sexual behavior in humans and animals, and for design of new categories of superagonists and antagonists. Extrapituitary effects by these new peptides may be observed on the central nervous system or reproductive organs of humans and animals that are different from those of LHRH. The latter will be especially true if some of these new peptides are found to be native peptides such as FSH-RH or the LHRH-like peptides that have been detected in the gonads that are yet to be identified. The reason for believing this projection is possible is that some of these peptides have high or unique LH and FSH releasing activity in the LHRH radioreceptor assay, as exemplified by the biological activities of peptide C.

10 Claims, No Drawings

EFFECTIVE PEPTIDES RELATED TO THE LUTEINIZING HORMONE RELEASING HORMONE FROM L-AMINO ACIDS

BACKGROUND OF THE INVENTION

Since the elucidation of the structure in 1971 of the luteinizing hormone releasing hormone (LHRH), the international chemical, biological and clinical research on this hormone has been enormous. A category of analogs which are more active than LHRH evolved from various investigators, but all have a D-amino acid in place of Gly[6], and have been known as "superagonists". Multiple citations to all this chemistry on LHRH are in "Advances in Reproductive Health Care, LHRH and Its Analogs Contraceptive and Therapeutic Applications", edited by B. H. Vickery, J. J. Nestor Jr., and E. S. E. Hafez, MTP Press Limited, (1984).

Retaining the L-configuration for each of the ten positions of LHRH, the literature (LHRH, listed by NICHD, Mar. 16, 1983), records more than 100 monosubstituted, and about 14 disubstituted analogs, all from naturally occurring amino acids, which have agonist activity, but apparently not one of these 114 analogs has been found to have agonist activity as potent as that of LHRH. Of these 114 agonist-analogs, [Ala[9]]-LHRH (LHRH, listed by NICHD, Mar. 16, 1983, No. 247) showed 65% activity in vitro, and [Phe[5]]-LHRH (Coy, D. H., Coy, E. J., Schally, A. V., *J. Med. Chem.* 16, 83 (1973)) showed 64% activity in vivo. [Trp[7]]-LHRH (E) was once found to have 80% activity in vivo, (Cone, B. S. et al., *Biochem. Biophys. Res. Commun.* 90, 1249 (1979)).

Two analogs, both of which contain an unnatural amino acid, were apparently equal to and better than LHRH, in vitro. These two analogs were [3(2-Nal)[3]]-LHRH (LHRH, listed by NICHD, Mar. 16, 1983, No. 82) and [N-MeLeu[7]]-LHRH (Ling, N., Vale, W., *Biochem. Biophys. Res. Commun.* 63, 801 (1975)), which were 200% and 100% as active as LHRH, in vitro, respectively, Apparently there has been no achievement of an agonist comparable to LHRH, i.e., equivalent potency for release of both LH and FSH, without substitutions with unnatural or the D-forms of natural amino acids.

The existence of a follicle stimulating hormone releasing hormone (FSHRH) has been both proposed and denied, and is still unresolved. Igarashi, M. and McCann, S. M., (*Endocrinology* 74, 446-452 (1964)) described the initial studies on a presumed FSHRH. Schwartz summarized physiological evidence which indicated that there must be some separate secretory control of FSH, (Folkers, K., Fuchs, S., Humphries, J., Wan, Y. P., and Bowers, C. Y., The Follicle Stimulating Hormone Releasing Hormone in *Novel Aspects of Reproductive Physiology*, Spilman, C. H., and Wilks, J. W., eds., Spectrum Publicatios, Inc., New York, 336 (1978)). The initial denials against FSHRH were made in 1970-71 by White, W. F., (*Hypophysiotropic Hormones of the Hypothalamus*, J. Meites, ed., The Williams and Wilkins Co., Baltimore, p. 248 (1970)), and by Schally, A. V., Arimura, A., Baba, Y., Nair, R. M. G., Matsuo, H., Redding, T. W., Debeljuk, L. and White, W. F., (*Biochem. Biophys. Res. Commun.* 43, 393 (1971)) and again by Matsuo, H., Baba, Y., Nair, R. M. G., Arimura, A. and Schally, A. V., (*Biochem. Biophys. Res. Commun.* 43, 1334 (1971)), and they stated—"one polypeptide regulates secretion of luteinizing and follicle stimulating hormones"—and they introduced the designation "gonadotropin releasing hormone" (GnRH), which has been widely used in endocrinology. Koch, Y., et al. (*Biochem. Biophys. Res. Commun.* 55, 623-629 (1973)) and Wise, P. M., et al. (*Endocrinology* 104, 940-947 (1979)) described results interpreted on the basis that LHRH is also FSHRH.

Several investigators described data on purification and bioassays in support of the existance of FSHRH. In 1973, Johanssen, K. N. G. et al., (*Biochem. Biophys. Res. Commun.* 50, 8-13 (1973)), Curry, B. L., et al. (*Biochem. Biophys. Res. Commun.* 50, 14-19 (1973)) and Bowers, C. Y., et al. (*Biochem. Biophys. Res. Commun.* 50, 20-26 (1973)) described fractions which released 40,000-128,000 ng/ml of FSH in comparison to synthetic LHRH which released ca. 18,000 ng/ml. Isarashi, M., et al. (Psychoneuroendocrinology. *Workshop Conf. Int. Soc. Phychoneuroendocrinology, Mieken*, Karger, Basel, 178-186 (1974)), Fawcett, C. P., et al. (*Endocrinology* 96, 1311-1314 (1975)), Yu, J. Y. L., et al. (*Life Sciences* 22, 269-282 (1978)), Yu, J. Y. L., et al. (*Neuroendocrinology* 29, 54-65 (1979)), and Blask, D. E., et al. (*Neuroendocrinology* 28, 36-43 (1979)), have all published results supporting the existance of FSHRH.

Fuchs, S., et al. (*Biochem. Biophys. Res. Commun.* 88, 92-96 (1979)) purified an entity, which unambiguously released FSH, was separated from [$^3$H]-LHRH and which appeared to have a molecular weight larger than that of LHRH, and which seemed not to be a prohormone of LHRH. Igarashi et al. (*Kitakanto Igaku.* 32(5) 409-421 (1982)), published a review of 29 publications on the existance of FSHRH as distinct from LHRH in porcine hypothalamus.

Concerning prohormonal forms of LHRH, Millar, R. P., et al. (*Colloq. Int. C.N.R.S.*, 487-510 (1978)), Millar, R. P., et al. (*Biochem. Biophys. Res. Commun.* 74, 720-731 (1977)), and King, J. A. and Millar, R. P., (*Science* 206, 67-69 (1979)) described important results.

Four naturally occuring LHRH's are now known as follows.

|  | 1 | 2 | 3 | 4 | 5 | 6 | 7 | 8 | 9 | 10 |
|---|---|---|---|---|---|---|---|---|---|---|
| Porcine/Ovine: | pGlu | His | Trp | Ser | Tyr | Gly | Leu | Arg | Pro | Gly—NH$_2$ |
| Salmon: | pGlu | His | Trp | Ser | Tyr | Gly | Trp | Leu | Pro | Gly—NH$_2$ |
| Chicken I: | pGlu | His | Trp | Ser | Tyr | Gly | Leu | Gln | Pro | Gly—NH$_2$ |
| Chicken II: | pGlu | His | Trp | Ser | His | Gly | Trp | Tyr | Pro | Gly—NH$_2$ |

Chicken I has Gln[8] for Arg[8] of the porcine/ovine LHRH. Chicken II has His[5] for Tyr[5], and Trp[7] Tyr[8] for Leu[7]Arg[8]. Salmon LHRH has Trp[7]Leu[8] for Leu[7]Arg[8] of the porcine/ovine LHRH. Chicken II and salmon LHRH have Trp[7], which is an aromatic substitution for the aliphatic Leu[7] of the porcine/ovine LHRH. Each of these four LHRH's may be presumed to have similar but specifically different receptors, but the differences may be so minor that any one of the four receptors might have some significant receptivity to accept any one of the three other LHRH's. The receptor for the porcine/ovine LHRH might effectively accept an antagonist with changes in positions 5, 8 and particularly 7, although Leu[7] is relatively non-functional compared to Trp[7].

Folkers, K., et al. (*Biochem. Biophys. Res. Commun.* 123(3), 1221-1226 (1984)) synthesized and assayed 13 antagonists having Trp[7] and one of these, [N-Ac-D-2-Nal[1], D-pClPhe[2], D-3-Pal[3], D-Arg[6], Trp[7], D-Ala[10]]-LHRH not only maintained antagonistic activity, but had increased potency (ca. 90% antiovulatory activity/250 ng; rats) in comparison with a companion analog with the Leu[7] of LHRH (58%).

On the basis of favoring the positive data from several investigators over several years on the existence of FSHRH, rather than the diverse negative data, and assigning special significance to the enhancement of antagonistic activity by having the Trp[7] of the chicken II and salmon LHRH's in place of Leu[7], a new approach was taken toward elucidation of the existence or not of FSHRH.

This new approach was as follows. Of the four known LHRH's, the differences are in positions 5, 7 and 8. His or Tyr occur in position 5, Leu or Trp occur in position 7, and Arg, Leu, Tyr and Gln occur in position 8 for a total involvment of six individual amino acids.

One possibility for the structure of the presumed FSHRH would be that it is a decapeptide with one or more of the same individual six amino acids, and in the same relative positions 5, 7 and 8. Upon this basis, there are a total of 16 possible peptides of which four are the recognized LHRH's. The remaining 12 peptides are as follows:

making only one change:
1. p-Glu His Trp Ser His Gly Leu Arg Pro Gly-NH$_2$
2. p-Glu His Trp Ser Tyr Gly Trp Arg Pro Gly-NH$_2$
3. p-Glu His Trp Ser Tyr Gly Leu Leu Pro Gly-NH$_2$
4. p-Glu His Trp Ser Tyr Gly Leu Tyr Pro Gly-NH$_2$ making two changes:
5. p-Glu His Trp Ser His Gly Leu Leu Pro Gly-NH$_2$
6. p-Glu His Trp Ser His Gly Leu Tyr Pro Gly-NH$_2$
7. p-Glu His Trp Ser His Gly Leu Gln Pro Gly-NH$_2$
8. p-Glu His Trp Ser Tyr Gly Trp Tyr Pro Gly-NH$_2$
9. p-Glu His Trp Ser Tyr Gly Trp Gln Pro Gly-NH$_2$
10. p-Glu His Trp Ser His Gly Trp Arg Pro Gly-NH$_2$ making three changes:
11. p-Glu His Trp Ser His Gly Trp Leu Pro Gly-NH$_2$
12. p-Glu His Trp Ser His Gly Trp Gln Pro Gly-NH$_2$ Two of these 12 peptides, numbers 2 and 3, are known, Cone, B. S., et al. (*Biochem. Biophys. Res. Commun.* 90, 1249 (1979)) and Yanaihara, N. et al. (*Biochem. Biophys. Res. Commun.* 49(5), 1280 (1972)), respectively. The remaining 10 peptides have been newly synthesized and the [Trp[7]]-LHRH has been resynthesized, and all of them were assayed in comparison with LHRH. The results are described herein.

We had considered that perhaps one of these 12 peptides might have remarkable hormonal activity in comparision with that of LHRH. Two of the 12 were considered to be unlikely to have biological interest, but there was no way to predict that even one of the remaining 10 would be biologically important, but it was considered that if just one were important on testing, such a result could be an important discovery. Unexpectedly, not only one, but two were discovered to be superior in potency and activity to LHRH, and three more, for a total of five, were comparable in activity to LHRH. We report the results of these syntheses and bioassays and state the diverse utilities herein.

THE INVENTION

It has been discovered, in accordance with the present invention, that five unpredictable decapeptides out of a total of twelve decapeptides possessed biological activities which are equivalent to or superior to those of LHRH, and which were never equaled by even one of about 114 peptides which were internationally synthesized and tested over about 14 years. Being equivalent to or superior to LHRH means that these five decapeptides release LH and/or FSH at least at one particular dose level and at least at one particular time, which are comparable to the release of LH and FSH by LHRH. These five of the twelve peptides are as follows:

A. p-Glu His Trp Ser His Gly Leu Arg Pro Gly-NH$_2$
B. p-Glu His Trp Ser His Gly Trp Arg Pro Gly-NH$_2$
C. p-Glu His Trp Ser His Gly Trp Gln Pro Gly-NH$_2$
D. p-Glu His Trp Ser His Gly Trp Leu Pro Gly-NH$_2$
E. p-Glu His Trp Ser Tyr Gly Trp Arg Pro Gly-NH$_2$

Of these five, decapeptide C is particularly unique, because the release of LH and FSH are dissociated activities in comparison to those of LHRH, and because the effectiveness of decapeptide C in a radioreceptor assay for LHRH is achieved at a level 46 times that of LHRH. It is considered reasonable that these highly active decapeptides, particularly peptides A and C, can exist in living species, but as yet undiscovered in tissues. To different degrees, these five decapeptides have essentially all of the diverse utilities of LHRH itself. Synthesis, deprotection and cleavage of the decapeptides, from the resin, were accomplished to yield the crude peptides which were then purified to yield the pure peptides, which were documented by analysis, and then bioassayed.

In accordance with the present invention, these decapeptides were synthesized and bioassayed as follows.

DETAILED DESCRIPTIONS OF PREFERRED EMBODIMENTS

| Abbreviations and Formulas | | |
|---|---|---|
| H$_2$O: water | HCl: hydrochloric acid | min: minute |
| DMF: dimethylformamide | Ala: alanine | sec: second |
| n-BuOH: n-butyl alcohol | Phe: phenylalanine | nm: nanometer |
| 2-PrOH: isopropyl alcohol | Glu: glutamic acid | cm: centimeter |
| EtOAc: ethyl acetate | Pyr: pyridine | mm: millimeter |
| BOC: t-butyloxycarbonyl | pGlu: pyroglutamic acid | TLC: thin layer chromotography |
| HF: hydrogen fluoride | His: histidine | |
| AC$_2$O: acetic anhydride | Trp: tryptophan | HPLC: high pressure liquid chromatography |
| HOAc: acetic acid | Ser: serine | |
| nBuOAc: n-butyl acetate | Tyr: tyrosine | meq/g: milliequivalent per gram |
| TFA: trifluoroacetic acid | Gln: glutamine | |
| CH$_3$CN: acetonitrile | Gly: glycine | ml/g: milliliter per |

| -continued |
| Abbreviations and Formulas |

| | | |
|---|---|---|
| Et₃N: triethylamine | Leu: leucine | gram |
| CH₂Cl₂: dichloromethane | Arg: arginine | |
| NH₄OAc: ammonium acetate | Pro: proline | |
| N—Me—Leu: N—Methylleucine | | KH₂PO₄: potassium phosphate |
| DIEA: diisopropylethylamine | | HOBT: 1-hydroxybenzotriazole |
| DCC: dicyclohexylcarbodiimide | | D-pCLPhe: D-parachlorophenylalanine |
| D-3-Pal: β-(3-Pyridyl)-D-alanine | | o-Cl—Z: o-chlorobenzyloxycarbonyl |
| D-2-Nal: 3-2(naphthyl)-D-alanine | | |
| Boc Gln—ONP: N—α-t-butyloxycarbonyl-L-Glutamine-p-nitro-phenylester | | |

The protected amino acids were purchased from Peninsula Laboratories, Inc., San Carlos, Calif. α-Amino functions were protected by the Boc-group. Side-chain functions were protected by tosyl for Arg and His; benzyl for Ser and dichlorobenzyl for Tyr. The benzhydrylamine hydrochloride resin was purchased from Beckman Inc., Palo Alto, Calif. All solvents (except TFA) were distilled before use. To test for homogeneity, the peptides were chromatographed on precoated TLC plates (silica gel, Merck, Darmstadt) in five of the following solvent systems:

| | | | |
|---|---|---|---|
| 1. | nBuOH=HOAc=pyr=H₂O=4:1:1:2 | 2. | EtOAc=pyr=HOAc=H₂O=20:5:3:3 |
| 3. | nBuOH=HOAc=H₂O=4:1:5(upper phase) | 4. | nBuOAc=nBuOH=HOAc=H₂O=2:8:2:3 |
| 5. | nBuOH=HOAc=EtOAc=H₂O=1:1:1:1 | 6. | EtOAc=pyr=HOAc=H₂O=5:5:1:3 |
| 7. | nBuOH=pyr=HOAc=H₂O=5:5:1:4 | 8. | nBuOH=HOAc=H₂O=4:1:2 |

The spots on the developed thin layer plates were detected with the chlorine o-tolidine reagent and Ehrlich reagent.

Program Sequence of Synthesis of the Peptides.

The peptides were synthesized by the solid phase method using a Beckman Model 990 Peptide Synthesizer. The benzhydrylamine hydrochloride resin (BHA-resin was used as a solid support. The program of the synthesizer was divided into subprograms to increase the versatility of the synthesizer, as follows.

(1.) Deprotection: 1. CH₂Cl₂ (2×wash, 1 min); 2. 50% TFA in CH₂Cl₂ containing 0.1% indole (1×wash, 1 min); 3. 50% TFA in CH₂CL₂ containing 0.1% indole (deprotection, 15 min); 4. CH₂Cl₂ (2×wash 1 min.).

(2.) Neutralization: 1. CH₂Cl₂ (2×wash, 1 min); 2. Et₃N (10% in CH₂Cl₂) or DIEA (5% CH₂Cl₂) (2×wash, 1 min); 3. Et₃N (10% in CH₂Cl₂) or DIEA (5% in CH₂Cl₂) (neutralization, 3 min); 4. CH₂Cl₂ (2×wash, 1 min).

(3.) DCC Coupling: 1. CH₂Cl₂ (2×wash, 1 min); 2. amino acid solution in CH₂Cl₂ (delivery, transfer, mix, 1 min); 3. DCC (10% in CH₂Cl₂), (delivery and mix, 180 min); 4. CH₂Cl₂ (2×wash, 1 min).

(4.) Active Ester Coupling: 1. CH₂Cl₂ (2×wash, 1 min); amino acid solution in DMF (delivery, transfer, mix 240 min); 3. CH₃Cl₂ (2×wash, 1 min).

(5.) Final wash: 1. CH₂Cl₂ (2×wash, 1 min); 2. 2-PrOH (3×wash, 1 min); 3. DMF (3×wash, 1 min); 4. CH₂Cl₂ (3×wash, 1 min).

(6.) Wash after TFA Treatment: 1. CH₂Cl₂ (2×wash, 1 min); 2. 2-PrOH (2×wash, 1 min); CH₂Cl₂ (3×wash, 1 min).

(7.) Acetylation: 1. CH₂Cl₂ (2×wash, 1 min); 2. 25% Ac₂O and 25% Pyr in CH₂Cl₂ (1×wash, 1 min); 3. 25% Ac₂O and 25% Pyr in CH₂Cl₂ (acetylation, 20 min); 4. CH₂Cl₂ (2×wash, 1 min).

The first amino acid was attached to the resin by the program sequence 2-3-5. Before placing the resin into the reaction vessel, it was allowed to swell in a separatory funnel with 25 ml of CH₂Cl₂/g resin for 1 hr. and washed once with the same amount of CH₂Cl₂ to remove the fine particles. In all couplings, a 3-4-fold excess of the Boc-amino acid over the nitrogen content of the resin (nitrogen content was about 0.5 meq/g dry resin) was usually used. This procedure generally resulted in a complete coupling reaction. If a positive ninhydrin color reaction was observed, a second coupling using an excess of the amino acid derivative was performed (program sequence 2-3-5). Then, the resin was acetylated (program sequence 2-7-5).

The next amino acid was attached by the program sequence 1-6-2-3-5. For DCC coupling, all amino acids were dissolved in a 40% DMF/CH₂Cl₂ solution together with 50 mg of HOBT, a/5 to 10 fold excess of DCC was added, and the general reaction time was 3 hours. Gln was coupled to the resin via its BocGlnONP derivative using the active ester coupling program sequence 1-6-2-4-5. The Boc-GlnONP was dissolved in DMF and a few mg of 1-hydroxybenzotriazole was added as a catalyst. The volume of the solvents and the reagents used for the washing and the performing of the chemical reactions was about 10 ml/g resin. The acetylation mixture was freshly prepared before each use.

For deprotections of the Boc-protected resin peptides after the attachement of Trp, 1,2-ethanedithiol, or thioanisole (2%) was added to the TFA deprotecting solution to protect Trp from decomposition. No HOBT was added as catalyst after the attachment of His to the resin-peptide to prevent inducing cleavage of the Tosyl protecting group on His.

Cleavage of the Peptides from the Resin

After all of the amino acids had been coupled, the peptide resin was dried overnight, in vacuo, by an oil pump. The resin was then treated with doubledistilled liquid hydrogen fluoride (10 ml/g resin) containing 10–25% distilled anisole and 10% of either 1,2-ethanedithiol or thioanisole for 45 minutes at 0° C. Then, the HF was evaporated under reduced pressure and the residue was dried overnight, in vacuo, by an oil pump. The mixture was then extracted twice with EtOAc (25 ml/g resin), and then three or four times with 30 ml 20% HOAc. The combined aqueous solution was lyophilized to yield the crude peptide.

Column Chromatography on Silica Gel.

150 to 200 mg of the crude peptide was applied to a column of silica gel (1×60 cm), which had been equilibrated with a solvent mixture of n-BuOH:HOAc:-H₂O=4:1:2, nBuOH=HOAc=H₂O=4:1:5 (upper phase) or nBuOH=pyr=HOAc=H₂O=4:1:1:2, and then the chromatography was done in the same solvent. Fractions of 1 to 2 ml were collected. The fractions were tested on TLC. The peptides, in general, were eluted in fractions 80–100. The fractions which contained the pure or nearly pure peptide were collected and lyophilized.

Preparative HPLC Purification.

The purest fraction of the desired peptide from column chromatography was further purified on a preparative HPLC column ($\mu$-Bondapak $C_{18}$, 7.8 mm×30 cm) with a HPLC system from Waters Associates, including a Solvent Programmer Model 660. The solvents employed were: Buffer A=0.1M $NH_4OAc$ pH=5, Buffer B=20% buffer A in $CH_3CN$. The peptide was eluted at a linear gradient of 20% to 80%; or 40% to 100% of buffer B in 20 min. at a flow rate of 2 ml/min. The desired peptide was collected and lyophilized to recover the pure peptide. The general recovery percentage was between 20 to 50%, depends on the purity of the column fraction.

The Determination of Purity and The Characterization.

The following procedures were used for determining the purity of all the synthetic analogs: high pressure liquid chromatography; thin layer chromatography in 5 solvents; and amino acid analysis.

Analytical HPLC was performed on a $\mu$-Bondapak $C_{18}$ column (3.9 mm×30 cm) with the same HPLC system from Waters Assoicates. The peptide was eluted at a linear gradient of 16 to 56% $CH_3CH$ in 15 min. at a flow rate of 2 ml/min. (buffer A=0.01M $KH_2PO_4$, pH 3.0; buffer B=20% buffer A in $CH_3CN$).

The TLC was performed on 0.25 mm silica gel plates 60 F-254 in the following systems:
1. nBuOH=HOAc=pyr=$H_2O$=4:1:1:2
2. EtOAc=pyr=HOAc=$H_2O$=20:5:3:3
3. nBuOH=HOAc=$H_2O$=4:1:5 (upper phase)
4. nBuOAc=nBuOH=HOAc=$H_2O$=2:8:2:3
5. nBuOH=HOAc=EtoAc=$H_2O$=1:1:1:1
6. EtoAc=pyr=HOAc=$H_2O$=5:5:1:3
7. nBuOH=pyr=HOAc=$H_2O$=5:5:1:4
8. nBuOH=HOAc=$H_2O$=4:1:2

Amino acid analysis.

The acid analysis was performed on a Beckman Model 119 Automatic Amino Acid Analyzer with a Hewlett Packard 3390A integrator. The peptides (0.3–0.5 mg) were hydrolized for 24 hours in a sealed glass tube at 110° C. in 6N HCl. The mixture was then dried, in vacuo. The residue was dissolved in sodium citrate buffer, pH 2.2 and 0.2 ml of the solution (200 nmole) was applied to the analyzer. Trp was not quantitatively analyzed.

Data (I) HPLC Analyses of the LHRH Analogs and LHRH

| No. | Structure | Retention time* |
|---|---|---|
| 1. | [His$^5$Tyr$^8$]—LHRH | 5'30" (min./sec.) |
| 2. | [Trp$^7$Tyr$^8$]—LHRH | 8'15" |
| 3. | [His$^5$Trp$^7$]—LHRH | 4'30" |
| 4. | [His$^5$Gln$^8$]—LHRH | 4'05" |
| 5. | [Trp$^7$Gln$^8$]—LHRH | 7'15" |
| 6. | [His$^5$Trp$^7$Gln$^8$]—LHRH | 5'46" |
| 7. | [His$^5$Leu$^8$]—LHRH | 6'20" |
| 8. | [His$^5$Trp$^7$Leu$^8$]—LHRH | 6'55" |
| 9. | [Trp$^7$]—LHRH | 7'01" |
| 10. | [His$^5$]—LHRH | 2'55" |
| 11. | [Tyr$^8$]—LHRH | 7'30" |
| 12. | [His$^5$Trp$^7$Tyr$^8$]—LHRH (chicken II) | 6'30" |
| 13. | LHRH (porcine) | 5'49" |
| 14. | [Trp$^7$Leu$^8$]—LHRH (salmon) | 9'10" |

*Solvent system - Linear gradient of 16 6o 56% $CH_3CH$ in 15 min. at a flow rate of 2 ml/min., (solvent A = 0.01 M $KH_2PO_4$, pH 3.0; solvent B = 20% A in $CH_3CN$) on a $\mu$-Bondapak $C_{18}$ column (3.9 mm × 30 cm, detection was done on a UV detector at 210 nm.) All compounds have purity better than 99%.

Data (II) Thin Layer Chromatogtaphy of LHRH Analogs

| No. | A | B | C | D | E | F | G | H |
|---|---|---|---|---|---|---|---|---|
| 1. | 0.55 | 0.10 | 0.09 | 0.12 | 0.87 | | | |
| 2. | 0.59 | 0.38 | 0.30 | 0.51 | 0.90 | | | |
| 3. | 0.32 | | | | 0.14 | 0.48 | 0.59 | 0.10 |
| 4. | 0.25 | 0.02 | 0.15 | 0.03 | 0.19 | | | |
| 5. | 0.39 | 0.09 | 0.22 | 0.11 | 0.60 | | | |
| 6. | 0.40 | 0.02 | 0.16 | 0.03 | 0.21 | | | |
| 7. | 0.76 | | 0.26 | 0.03 | 0.49 | | | 0.29 |
| 8. | 0.42 | | 0.24 | 0.03 | 0.61 | | | 0.28 |
| 9. | 0.53 | 0.02 | 0.17 | 0.06 | 0.56 | | | |
| 10. | 0.32 | | | | 0.11 | 0.48 | 0.59 | 0.11 |
| 11. | 0.49 | | | | 0.66 | 0.70 | 0.79 | 0.50 |
| 14. | 0.67 | | | 0.10 | 0.66 | | | 0.33 |

A = nBuOH=HOAc=Pyridine=$H_2O$=4:1:1:2
B = EtOAc=Pyridine=HOAc=$H_2O$=20:5:3:3
C = nBuOH=HOAc=$H_2O$=4:1:5 (upper phase)
D = nBuOAc=nBuOH=HOAc=$H_2O$=2:8:2:3
E = nBuOH=HOAc=EtOAc=$H_2O$=1:1:1:1
F = EtOAc=Pyridine=HOAc=$H_2O$=5:5:1:3
G = nBuOH=Pyridine=HOAc=$H_2O$=5:5:1:4
H = nBuOH=HOAc=$H_2O$=4:1:2

Data (III) Amino Acid Analyses$^a$ of LHRH Analogs

| No. | Ser | Glu | Pro | Gly | Leu | Tyr | His | Trp | Arg |
|---|---|---|---|---|---|---|---|---|---|
| 1. | 0.91 | 1.05 | 1.07 | 2.03 | 1.03 | 1.05 | 1.88 | + | |
| 2. | 0.86 | 1.03 | 1.14 | 2.00 | | 2.05 | 0.92 | ++ | |
| 3. | 0.82 | 1.10 | 1.10 | 2.02 | | | 1.97 | ++ | 0.99 |
| 4. | 0.82 | 2.06 | 1.12 | 1.99 | 0.96 | | 2.06 | + | |
| 5. | 0.82 | 2.07 | 1.01 | 2.01 | | 1.09 | 0.99 | ++ | |
| 6. | 0.77 | 2.05 | 1.13 | 1.95 | | | 2.10 | ++ | |
| 7. | 0.82 | 1.01 | 1.07 | 2.02 | 2.06 | | 2.03 | + | |
| 8. | 0.83 | 0.99 | 1.08 | 2.04 | 0.99 | | 2.07 | ++ | |
| 9. | 0.92 | 1.07 | 1.10 | 1.99 | | 1.03 | 0.93 | ++ | 0.97 |
| 10. | 0.92 | 1.07 | 1.10 | 2.00 | 1.03 | | 1.90 | + | 0.99 |
| 11. | 0.90 | 1.04 | 1.08 | 1.95 | | 2.07 | 0.94 | + | |
| 12$^b$. | 0.89 | 0.93 | 1.03 | 2.04 | | 0.87 | 1.98 | 1.86 | |
| 13$^b$. | 0.98 | 0.93 | 0.87 | 2.09 | 1.14 | 1.07 | 0.93 | 1.03 | 1.11 |
| 14. | 0.84 | 1.06 | 1.06 | 2.01 | 1.01 | 1.03 | 0.97 | ++ | |

$^a$All hydrolyses were performed in evacuated sealed tubes with 6N HCl at 110° C. for 24 h.
$^b$Peptides 12 and 13 were purchased from Peninsula Laboratories (Belmont, CA.). These are the data given by Peninsula.

CHEMICAL RESULTS AND HORMONAL ACTIVITIES

The activities of the four natural LHRH's are in Table I. The salmon-LHRH and chicken I-LHRH have extremely low activities to release LH and FSH. The chicken II-LHRH has about $\frac{1}{3}$ of the activities of LHRH to release LH and FSH.

TABLE I

| Activities of the Four Natural LHRH's | | |
|---|---|---|
| P/O LHRH | 100% | 100% |
| [Trp$^7$,Leu$^8$]—LHRH (salmon) | 2–3% (a) | — |
| [Leu$^7$,Gln$^8$]—LHRH (chicken I) | 3.4% (b) | 3.2% (b) |

TABLE I-continued

Activities of the Four Natural LHRH's

| [His⁵,Trp⁷,Tyr⁸]—LHRH (chicken II)* | 32 (b) | 41% (b) |

(a) The synthetic salmon Gn-RH was found to posess 2-3% of the potency of P/O LHRH to stimulate secretion of LH by rat anterior pituitary cells in primary culture, Sherwood et al. (Proc. Natl. Acad. Sci. U.S.A. 80, 2794-2798, 1983).
(b) These percentages were reported by Miyamoto et al. (Proc. Natl. Acad. Sci. U.S.A. 81, 3874-3878, 1984), for the release of LH and FSH, in vitro, with rat pituitary cells.
*In our assays, the chicken II-peptide showed an 18% and a 30% release of LH at dose levels in rats of 100 and 1000 ng, respectively. The corresponding release of FSH was 62% and 86% at the same two dose levels respectively.

Not one of the salmon and two chicken-LHRH's are attractive for practical utility in the human.

The data on the release of LH and FSH in rats by modifications of LHRH with one structural change are in Table II.

[His⁵]-LHRH and [Trp⁷]-LHRH were as active as LHRH at two dose levels for the release of LH. [His⁵]-LHRH was twice as active as LHRH at the high dosage for the release of FSH, [Trp⁷]-LHRH was as active as LHRH for the release of FSH.

Consequently, [His⁵]-LHRH is as important as LHRH for the release of LH and can selectively release more FSH then LHRH. On this basis, [His⁵]-LHRH could be more important than [Trp⁷]-LHRH. [Trp⁷]-LHRH has been previously described in the literature, Cone et al. (*Biochem. Biophys. Res. Commun.* 90, 1249 (1979)).

[Leu⁸]-LHRH and [Tyr⁸]-LHRH had relatively low activities to release LH and FSH.

Table III contains the data on the modifications of LHRH with two structural changes.

Exclusive of the salmon-LHRH, only one of the six decapeptides with two structural changes had significant activity. This peptide [His⁵Trp⁷]-LHRH was as active as LHRH for the release of both LH and FSH, when monitored 60 minutes after subcutaneous injection of dose levels of 300 and 3000 ng.

When monitored 30 minutes after injection at levels of 50 and 100 ng of [His⁵Trp⁷]-LHRH, the released levels of LH were significantly positive, but less than that at the higher dosage, and the level of FSH released at 50 ng was equivalent to that from LH. In a companion experiment, [His⁵Trp⁷]-LHRH released significantly more LH and FSH than did LHRH at a dosage of 50 ng. When monitored 15 minutes after injection, [His⁵Trp⁷]-LHRH at a dosage level of 100 ng released levels of LH and FSH which were equivalent to that released by the same dosage of LHRH.

Table IV contains the data on the release of LH and FSH in rats by modification of LHRH with three structural changes. At dosage levels of 300 and 3000 ng, [His⁵Trp⁷Gln⁸]-LHRH released less LH, but as much FSH at the higher dosage of 3000 ng as LHRH, when monitored 60 minutes after subcutaneous injection. [His⁵Trp⁷Gln⁸]-LHRH at dosage levels of 100 and 1000 ng released equivalent levels of LH and FSH when monitored 15 minutes after injection.

[His⁵Trp⁷Leu⁸]-LHRH, at levels of 100 and 1000 ng released up to 50% of the LH released by LHRH, but was equivalent in activity to LHRH for the release of FSH.

SUMMARY OF IN VIVO ASSAY RESULTS

The data in Tables II, III and IV, which show that some of these decapeptides release as much or more LH and FSH than LHRH are consolidated in Table V, and with the exclusion of those peptides which release less LH and FSH.

Of these peptides with one structural change, [His⁵]-LHRH was equivalent to LHRH in the release of LH and was two times as effective in the release of FSH at the higher dose level. [Trp⁷]-LHRH was equivalent to LHRH in the release of both LH and FSH.

Of those peptides with two structural changes, only one has significant activity. This peptide, [His⁵Trp⁷]-LHRH was as active as LHRH for the release of both LH and FSH, when monitored 60 minutes after subcutaneous injection of dose levels of 300 and 3000 ng. When monitored 30 minutes after injection of levels of 50 and 1000 ng, the levels of released LH were significantly positive, but lower than that released at the higher dose level, and the released level of FSH was higher than that for LH. The release of FSH appeared favored. When monitored 15 minutes after injection of 100 and 1000 ng levels of [His⁵Trp⁷]-LHRH and LHRH, it was evident that both peptides had comparable activities.

Of those peptides with three structural changes, [His⁵Trp⁷Gln⁸]-LHRH was as effective at 100 ng as LHRH for the release of LH, and was about two times as effective as [His⁵, Trp⁷Leu⁸]-LHRH for the release of LH. Both of these peptides, at dosages of 100 and 1000 ng released as much FSH as LHRH. The differential in activity for the release of FSH favored [His⁵Trp⁷Leu⁸]-LHRH over [His⁵Trp⁷Gln⁸]-LHRH.

Data from Radio Receptor Assays.

Data are included in Table II, III, IV and V from radio receptor assays as described by Heber et al. (*Am. J. Physiol.* 325(2): E227–E230 (1978)).

For the radio receptor assay, labelled $^{125}$I-D-Lys⁶-LHRH, was utilized as the ligand. The results are expressed as the relative inhibitory binder of the analog to LHRH at $ID_{50}$ values. RRA values of 1:1 indicate the analog and LHRH compete equally for the receptor while 46:1 indicates the analog competes much less effectively for the receptor since its $ID_{50}$ is 46 and LHRH is 1.

The five peptides which, in at least one assay at one dose level and at one time of monitoring, release as much or more LH and/or FSH as LHRH are listed in Table VI and in order of descending values of $ID_{50}$.

Peptides 1 and 2 of Table VI do not have Arg⁸, but have Gln⁸ and Leu⁸, and greater concentrations of peptides 1 and 2 are required in the assay to provide a 50% level of inhibition. These results clearly indicate that in tissue there is very likely a different receptor for such a peptide without Arg⁸ in contrast to the receptor which has been identified with LHRH which has Arg⁸. Peptides 3, 4 and 5 of Table VI have activities in the assay expressed by values less than 1:1, which means that peptides 3, 4 and 5, all of which do have Arg⁸, are inhibiting like LHRH in the receptor identified with LHRH.

TABLE VI

Summary of $ID_{50}$ Data.

| Peptide | $ID_{50}$ nM |
|---|---|
| 1. [His⁵Trp⁷Gln⁸]—LHRH | 46:1 |
| 2. [His⁵Trp⁷Leu⁸]—LHRH | 12:1 |
| 3. [His⁵Trp⁷]—LHRH | 0.7:1 |
| 4. [Trp⁷]—LHRH | 0.6:1 |
| 5. [His⁵]—LHRH | 0.4:1 |

It is understandable that there can be one receptor for an $Arg^8$-LHRH and another receptor for a peptide with a different amino acid in place of Arg in position 8. Arg is a uniquely functional amino acid.

The peptides in Table VII have been found to have somewhat lower or very significantly lower activities to release LH and FSH in comparison with those activities of LHRH. Therefore, these peptides range from moderate to very weak agonists in comparison with LHRH, and it is to be expected that relatively high concentrations of these agonists would be required to inhibit [D-$Lys^6$]-LHRH in the receptor binding assay. Consequently, the $ID_{50}$ values of Table VII for peptides weaker in agonist activity than that of LHRH do not have the same biological significance as the $ID_{50}$ values in Table VI for those peptides which have agonist activity equivalent to or greater than that of LHRH.

TABLE VII

| Peptide | $ID_{50}$ nM |
|---|---|
| 1. [$Gln^8$]—LHRH | 358:1 |
| 2. [$Trp^7Glu^8$]—LHRH | 133:1 |
| 3. [$His^5Gln^8$]—LHRH | 106:1 |
| 4. [$Trp^7Leu^8$]—LHRH | 46:1 |
| 5. [$Trp^7Tyr^8$]—LHRH | 28:1 |
| 6. [$His^5Leu^8$]—LHRH | 26:1 |
| 7. [$Tyr^8$]—LHRH | 26:1 |
| 8. [$His^5Tyr^8$]—LHRH | 8:1 |
| 9. [$His^5Trp^7Tyr^8$]—LHRH | 5:1 |

Summary of $ID_{50}$ Data.

Perhaps, the most important aspect of the data in Tables VI and VII is that the inhibitory activity of peptides 1 and 2 of Table VI is greatly different from that of peptides 3, 4 and 5 in the common receptor assay. This aspect clearly indicates a different receptor for peptides 1 and 2 which do not have Arg in position 8.

UTILITY

The ovine/porcine luteinizing hormone releasing hormone has been known for a decade to have diverse medical usefulness. The longer this hormone is studied in endocrinology and in medicine, the more uses are uncovered. In the early days, the utility of LHRH was essentially in fields of reproduction. Recently, utilities to treat hormone influenced tumors, such as prostatic cancer and mammary cancer, have been uncovered.

More specifically, LHRH therapy has been important for hypogonadotropic hypogonadal men. Infertility in the male has been corrected with LHRH and its agonists. LHRH has been used for the therapy of precocious puberty.

In the cancer field, LHRH analogs have been used for mammary carcinoma and prostatic carcinoma and positive clinical data are now known.

LHRH has diagnostic uses and it has applications in veterinary medicine.

The new peptides of this invention, particularly the following five,
A. p-Glu His Trp Ser His Gly Leu Arg Pro Gly-$NH_2$
B. p-Glu His Trp Ser His Gly Trp Arg Pro Gly-$NH_2$
C. p-Glu His Trp Ser His Gly Trp Gln Pro Gly-$NH_2$
D. p-Glu His Trp Ser His Gly Trp Leu Pro Gly-$NH_2$
E. p-Glu His Trp Ser Tyr Gly Trp Arg Pro Gly-$NH_2$
have activities to release LH and FSH which are equal to or higher than that of LHRH (ovine-porcine).

Consequently, it is certain that these new peptides will have the same diverse utilities for hypogonadotropic hypogonadal men, and for infertility in the male, and for precocious puberty, and for mammary carcinoma and prostatic carcinoma, although to different degrees.

These new peptides will also be useful to develop assay methods for diagnostic purposes and for applications in veterinary medicine.

Those new peptides of lower activities than those of LHRH will also be useful for the design of modifications with D-amino acids which will increase their biological potencies.

It is projected that one or more of these new peptides could be found to exist in a tissue of mammalian species as the research continues in the next few years. The finding of anyone of these new peptides in tissue would greatly increase its importance, which is already of high priority in endocrinology.

Tables II-VII

TABLE II

Release of LH and FSH in Rats by Modification of LHRH with One Structural Change Release 60 min. after sc injection

| | LH ng/ml | | | | LH % change | | FSH ng/ml | | | | FSH % change | | RRA |
|---|---|---|---|---|---|---|---|---|---|---|---|---|---|
| | Dosage of Peptide | | | | | | Dosage of Peptide | | | | | | |
| Peptides | 300 ng | P | 3000 ng | P | 300 ng | 3000 ng | 300 ng | P | 3000 ng | P | 300 ng | 3000 ng | $ID_{50}$ nM |
| Saline | 0.25 ± 0.02 | <.001 | | | | | 199 ± 28 | <.001 | | | | | |
| LHRH | 11 ± 1.6 | — | 82 ± 8 | — | 100 | 100 | 596 ± 40 | — | 1173 ± 146 | — | 100 | 100 | |
| [$Gln^8$]—LHRH* | — | — | 5.5 ± 0.67 | <0.001 | — | 7 | — | — | 465 ± 50 | <0.001 | — | 49 | 385:1 |
| [$His^5$]—LHRH | 14 ± 2.3 | NS | 142 ± 29 | NS | NS | 173 | 652 ± 66 | NS | 2684 ± 434 | <0.01 | NS | 229 | 0.4:1 |
| [$Trp^7$]—LHRH | 14.5 ± 2.4 | NS | 115 ± 19 | NS | NS | 140 | 543 ± 68 | NS | 1259 ± 70 | NS | NS | NS | 0.6:1 |
| [$Leu^8$]—LHRH** | — | — | — | — | — | — | — | — | — | — | — | — | — |
| [$Tyr^8$]—LHRH | 2.5 ± 0.22 | <0.001 | 2.7 ± 0.21 | <0.001 | 23 | 3 | 285 ± 35 | <0.001 | 449 ± 31 | <0.001 | 48 | 38 | 26:1 |

Release 30 min. after sc injection

| | LH ng/ml | | | | LH % change | | FSH ng/ml | | | | FSH % change | | RRA |
|---|---|---|---|---|---|---|---|---|---|---|---|---|---|
| | Dosage of Peptide | | | | | | Dosage of Peptide | | | | | | |
| Peptides | 100 ng | P | 1000 ng | P | 100 ng | 1000 ng | 100 ng | P | 1000 ng | P | 100 ng | 1000 ng | $ID_{50}$ nM |

TABLE II-continued

Release of LH and FSH in Rats by Modification of LHRH with One Structural Change

| | | | | | | | | | | | | |
|---|---|---|---|---|---|---|---|---|---|---|---|---|
| LHRH | 11 ± 1 | — | 46 ± 9 | — | 100 | 100 | 494 ± 48 | — | 691 ± 134 | — | 100 | 100 |
| [Gln$^8$]—LHRH* | 0.6 ± 0.1 | <0.001 | 7 ± 0.8 | <0.01 | 5.5 | 15.2 | 284 ± 36 | <0.01 | 396 ± 60 | NS | 58 | 57 | 358:1 |

*Chicken I LHRH
**Inactive at 1000 and 5000 ng for both LH and FSH

TABLE III

Release of LH and FSH in Rats by Modification of LHRH with Two Structural Changes

Release 60 min. after sc injection

| | LH ng/ml | | | | LH % change | | FSH ng/ml | | | | FSH % change | | RRA |
|---|---|---|---|---|---|---|---|---|---|---|---|---|---|
| | Dosage of Peptide | | | | | | Dosage of Peptide | | | | | | |
| Peptides | 300 ng | P | 3000 ng | P | 300 ng | 3000 ng | 300 ng | P | 3000 ng | P | 300 ng | 3000 ng | ID$_{50}$ nM |
| Saline | 0.25 ± 0.02 | | | | | | 199 ± 28 | | | | | | |
| LHRH | 11 ± 1.6 | | 82 ± 8 | | 100 | 100 | 596 ± 40 | | 1173 ± 146 | | 100 | 100 | |
| [Trp$^7$Leu$^8$]—LHRH** | — | — | 2.5 ± 0.34 | <0.001 | — | 3.0 | — | — | 258 ± 25 | <0.001 | — | 22 | 46:1 |
| [His$^5$Leu$^8$]—LHRH | 2.2 ± 0.8 | <0.001 | 1.8 ± 0.3 | <0.001 | 20 | 2.2 | 261 ± 30 | <0.001 | 205 ± 7 | <0.001 | 44 | 18 | 26:1 |
| [His$^5$Tyr$^8$]—LHRH | — | — | 2.8 ± 0.31 | <0.001 | — | 3.4 | — | — | 495 ± 48 | <0.001 | — | 42 | 8:1 |
| [His$^5$Gln$^8$]—LHRH | 3.3 ± 0.21 | <0.001 | 6.8 ± 0.85 | <0.001 | 30 | 8.3 | 283 ± 16 | <0.001 | 456 ± 36 | <0.001 | 48 | 39 | 106:1 |
| [Trp$^7$Tyr$^8$]—LHRH | 2.8 ± 0.31 | <0.001 | 3.8 ± 0.31 | <0.001 | 25 | 4.6 | 209 ± 21 | <0.001 | 352 ± 49 | <0.001 | 35 | 30 | 28:1 |
| [Trp$^7$Gln$^8$]—LHRH | 3.2 ± 0.31 | <0.001 | 7.5 ± 1.4 | <0.001 | 29 | 9.1 | 345 ± 48 | <0.001 | 474 ± 70 | 0.001 | 58 | 40 | 133:1 |
| LHRH | 17 ± 2.3 | | 113 ± 27 | | | | 554 ± 32 | | 1501 ± 158 | | | | |
| [His$^5$Trp$^7$]—LHRH | 26.0 ± 4.1 | NS | 138 ± 19 | NS | NS | NS | 624 ± 41 | NS | 1448 ± 123 | NS | NS | NS | 0.7:1 |

Release 30 min. after sc injection

| | LH ng/ml | | | | LH % change | | FSH ng/ml | | | | FSH % change | | RRA |
|---|---|---|---|---|---|---|---|---|---|---|---|---|---|
| | Dosage of Peptide | | | | | | Dosage of Peptide | | | | | | |
| Peptides | 50 ng | P | 1000 ng | P | 50 ng | 1000 ng | 50 ng | P | 1000 ng | P | 50 ng | 1000 ng | ID$_{50}$ nM |
| Saline | 0.12 ± 0.01 | <.001 | | | | | 249 ± 26 | <.02 | | | | | |
| LHRH | 18 ± 1.5 | — | 128 ± 7 | — | 100 | 100 | 515 ± 97 | — | 1010 ± 97 | — | 100 | 100 | |
| [His$^5$Tyr$^8$]—LHRH | 0.5 ± 0.4 | <0.001 | 5.0 ± 0.7 | <0.001 | 3 | 4 | 235 ± 51 | NS | 534 ± 104 | 0.02 | NS | 3 | 8:1 |
| [His$^5$Trp$^7$]—LHRH | 12 ± 1 | <0.01 | 51 ± 3 | <0.001 | 67 | 40 | 387 ± 81 | NS | 857 ± 86 | NS | NS | NS | 0.7:1 |

Release 15 min. after sc injection

| | LH ng/ml | | | | LH % change | | FSH ng/ml | | | | FSH % change | | RRA |
|---|---|---|---|---|---|---|---|---|---|---|---|---|---|
| | Dosage of Peptide | | | | | | Dosage of Peptide | | | | | | |
| Peptides | 50 ng | P | 1000 ng | P | 50 ng | 1000 ng | 50 ng | P | 1000 ng | P | 50 ng | 1000 ng | ID$_{50}$ nM |
| Saline | 0.13 ± 0.01 | <.001 | | | | | 257 ± 22 | | | | | | |
| LHRH | 16 ± 2 | — | | | 100 | | 550 ± 56 | | | | 100 | | |
| [His$^5$Trp$^7$]—LHRH | 30 ± 3 | <0.001 | 39 ± 4 | | 188 | | 663 ± 128 | 0.01 | 562 ± 126 | | 121 | | 0.7:1 |

| | LH ng/ml | | | | LH % change | | FSH ng/ml | | | | FSH % change | | RRA |
|---|---|---|---|---|---|---|---|---|---|---|---|---|---|
| | Dosage of Peptide | | | | | | Dosage of Peptide | | | | | | |
| Peptides | 100 ng | P | 1000 ng | P | 100 ng | 1000 ng | 100 ng | P | 1000 ng | P | 100 ng | 1000 ng | ID$_{50}$ nM |
| Saline | 0.17 ± 0.5 | <.001 | | | | | 237 ± 18 | .001 | | | | | |
| LHRH* | 21 ± 4 | | 39 ± 8 | | 100 | 100 | 455 ± 65 | | 576 ± 58 | | 100 | | |
| LHRH | 24 ± 4 | — | 57 ± 7 | — | 100 | 100 | 465 ± 49 | | 483 ± 44 | — | 100 | 100 | |
| [His$^5$Trp$^7$]—LHRH* | 13 ± 1.3 | NS | 23 ± 2 | <.001 | NS | 59 | 346 ± 18 | NS | 456 ± 57 | NS | NS | NS | 0.7:1 |
| [His$^5$Leu$^8$]—LHRH | 0.2 ± 0.01 | <.001 | 3.3 ± 0.05 | <.001 | 0.8 | 5 | 202 ± 24 | .001 | 276 ± 18 | .001 | 43 | 57 | 26:1 |

TABLE III-continued
Release of LH and FSH in Rats by Modification of LHRH with Two Structural Changes

| | | | | | | | | | | | | | |
|---|---|---|---|---|---|---|---|---|---|---|---|---|---|
| [His$^5$Gln$^8$]—LHRH | 7 ± 0.9 | .001 | 27 ± 3 | <.01 | 29 | 47 | 343 ± 37 | NS | 416 ± 30 | NS | NS | NS | 106:1 |
| [His$^5$Trp$^7$]—LHRH | 30 ± 4 | NS | 78 ± 13 | NS | NS | NS | 502 ± 56 | NS | 429 ± 53 | NS | NS | NS | 0.7:1 |
| [Trp$^7$Gln$^8$]—LHRH | 7 ± 0.8 | 34 ± 4 | <.02 | 29 | 60 | 421 ± 42 | NS | 502 ± 57 | NS | NS | NS | 133:1 |

**Salmon—LHRH

TABLE IV
Release of LH and FSH in Rats by Modification of LHRH with Three Structural Changes

Release 60 min. after sc injection

| | LH ng/ml Dosage of Peptide | | | | LH % change Dosage of Peptide | | FSH ng/ml Dosage of Peptide | | | | FSH % change Dosage of Peptide | | RRA |
|---|---|---|---|---|---|---|---|---|---|---|---|---|---|
| | 300 ng | P | 3000 ng | P | 300 ng | 3000 ng | 300 ng | P | 3000 ng | P | 300 ng | 3000 ng | ID$_{50}$ nM |
| Saline | 0.25 ± 0.02 | <0.001 | — | | | | 199 ± 28 | <0.001 | | | | | |
| LHRH | 11 ± 1.6 | — | 82 ± 8 | — | 100 | 100 | 596 ± 40 | — | 1173 ± 146 | — | 100 | 100 | |
| [His$^5$Trp$^7$Gln$^8$]—LHRH | 5 ± 0.6 | <0.01 | 53 ± 8.6 | <0.05 | 46 | 65 | 404 ± 16 | ~0.001 | 1161 ± 119 | NS | 68 | NS | 46:1 |
| [His$^5$Trp$^7$Tyr$^8$] (Chicken II) | 3.5 ± 0.22 | <0.001 | 8.4 ± 0.68 | <0.001 | 32 | 10 | 344 ± 41 | ~0.001 | 644 ± 44 | <0.001 | 58 | 55 | 5:1 |
| [His$^5$Trp$^7$Leu$^8$]—LHRH | 2.5 ± 0.2 | <0.001 | 5 ± 0.25 | <0.001 | 23 | 6 | 369 ± 35 | ~0.001 | 376 ± 69 | <0.001 | 62 | 32 | 12:1 |

Release 30 min. after sc injection

| | Dosage of Peptide | | | | | | Dosage of Peptide | | | | | | |
|---|---|---|---|---|---|---|---|---|---|---|---|---|---|
| | 100 ng | P | 1000 ng | P | 100 ng | 1000 ng | 100 ng | P | 1000 ng | P | 100 ng | 1000 ng | ID$_{50}$ nM |
| LHRH | 11 ± 1 | — | 46 ± 9 | — | 100 | 100 | 434 ± 48 | — | 691 ± 134 | — | 100 | 100 | |
| [His$^5$Trp$^7$Tyr$^8$] (Chicken II) | 2 ± 0.4 | <0.001 | 14 ± 2 | <0.01 | 18 | 39 | 305 ± 26 | <0.05 | 596 ± 82 | NS | 62 | NS | 5:1 |

Release 15 min. after sc injection

| | Dosage of Peptide | | | | | | Dosage of Peptide | | | | | | |
|---|---|---|---|---|---|---|---|---|---|---|---|---|---|
| | 100 ng | P | 1000 ng | P | 100 ng | 1000 ng | 100 ng | P | 1000 ng | P | 100 ng | 1000 ng | ID$_{50}$ nM |
| Saline | 0.9 ± 0.7 | <0.001 | | | | | 250 ± 21 | 0.001 | | | | | |
| LHRH | 24 ± 4 | — | 57 ± 7 | — | 100 | 100 | 465 ± 49 | — | 483 ± 84 | — | 100 | 100 | |
| [His$^5$Trp$^7$Gln$^8$]—LHRH | 17 ± 3 | NS | 66 ± 15 | NS | NS | NS | 403 ± 45 | NS | 486 ± 17 | NS | NS | NS | 46:1 |
| [His$^5$Trp$^7$Leu$^8$]—LHRH | 9 ± 1 | <.01 | 23 ± 3 | <.001 | 38 | 40 | 383 ± 48 | NS | 445 ± 33 | NS | NS | NS | 5:1 |

TABLE V
Release of LH and FSH in Rats by Modifications of LHRH with One, Two and Three Structural Changes

Release 60 min. after sc injection

| Peptides | LH ng/ml Dosage of Peptide | | | | LH % change | | FSH ng/ml Dosage of Peptide | | | | FSH % change | | RRA |
|---|---|---|---|---|---|---|---|---|---|---|---|---|---|
| | 300 ng | P | 3000 ng | P | 300 ng | 3000 ng | 300 ng | P | 3000 ng | P | 300 ng | 3000 ng | ID$_{50}$ nM |
| LHRH | 11 ± 1.6 | — | 82 ± 8 | — | 100 | 100 | 596 ± 40 | — | 1173 ± 146 | — | 100 | 100 | |
| [His$^5$]—LHRH | 14 ± 2.3 | NS | 142 ± 29 | NS | NS | NS | 652 ± 66 | NS | 2684 ± 434 | <0.01 | NS | 229 | 0.4:1 |
| [Trp$^7$]—LHRH | 14.5 ± 2.4 | NS | 115 ± 19 | NS | NS | NS | 543 ± 68 | NS | 1259 ± 70 | NS | NS | NS | 0.6:1 |

Release 60 min. after sc injection

| Peptides | LH ng/ml Dosage of Peptide | | | | LH % change | | FSH ng/ml Dosage of Peptide | | | | FSH % change | | RRA |
|---|---|---|---|---|---|---|---|---|---|---|---|---|---|
| | 300 ng | P | 3000 ng | P | 300 ng | 3000 ng | 300 ng | P | 3000 ng | P | 300 ng | 3000 ng | ID$_{50}$ nM |
| LHRH | 17 ± 2.3 | | 113 ± 27 | | 100 | 100 | 596 ± 40 | | 1173 ± 146 | | 100 | 100 | |
| [His$^5$Trp$^7$]—LHRH | 26.0 ± | NS | 138 ± | NS | NS | NS | 624 ± | NS | 1448 ± | NS | NS | NS | 0.7:1 |

TABLE V-continued

Release of LH and FSH in Rats by Modifications of LHRH with One, Two and Three Structural Changes 4.1  19  41  123

| | Release 30 min. after sc injection | | | | | | | | | | |
|---|---|---|---|---|---|---|---|---|---|---|---|
| | LH ng/ml | | | | LH % change | | FSH ng/ml | | | | FSH % change | |
| | Dosage of Peptide | | | | | | Dosage of Peptide | | | | | RRA |
| | 50 ng | P | 1000 ng | P | 50 ng | 1000 ng | 50 ng | P | 1000 ng | P | 50 ng | 1000 ng | ID$_{50}$ nM |
| LHRH | 18 ± 1.5 | — | 128 ± 7 | — | 100 | 100 | 515 ± 97 | — | 1010 ± 97 | — | 100 | 100 | |
| [His$^5$Trp$^7$]—LHRH | 12 ± 1 | <0.001 | 51 ± 3 | <0.001 | 67 | 40 | 387 ± 81 | NS | 857 ± 86 | <0.001 | NS | 85 | 0.7:1 |

| | Release 15 min. after sc injection | | | | | | | | | | | |
|---|---|---|---|---|---|---|---|---|---|---|---|---|
| | LH ng/ml | | | | LH % change | | FSH ng/ml | | | | FSH % change | |
| | Dosage of Peptide | | | | | | Dosage of Peptide | | | | | RRA |
| | 100 ng | P | 1000 ng | P | 100 ng | 1000 ng | 100 ng | P | 1000 ng | P | 100 ng | 1000 ng | ID$_{50}$ nM |
| LHRH* | 21 ± 4 | | 39 ± 8 | | 100 | 100 | 455 ± 65 | | 576 ± 58 | | 100 | | |
| LHRH | 24 ± 4 | — | 57 ± 7 | — | 100 | 100 | 465 ± 49 | — | 483 ± 44 | — | 100 | 100 | |
| [His$^5$Trp$^7$]—LHRH* | 13 ± 1.3 | NS | 23 ± 2 | <.001 | NS | 59 | 346 ± 18 | NS | 456 ± 57 | NS | NS | NS | 0.7:1 |
| [His$^5$Trp$^7$]—LHRH | 30 ± 4 | NS | 78 ± 13 | NS | NS | NS | 502 ± 56 | NS | 429 ± 53 | NS | NS | NS | 0.7:1 |

| | Release 60 min. after sc injection | | | | | | | | | | | |
|---|---|---|---|---|---|---|---|---|---|---|---|---|
| | LH ng/ml | | | | LH % change | | FSH ng/ml | | | | FSH % change | |
| | Dosage of Peptide | | | | | | Dosage of Peptide | | | | | RRA |
| Peptides | 300 ng | P | 3000 ng | P | 300 ng | 3000 ng | 300 ng | P | 3000 ng | P | 300 ng | 3000 ng | ID$_{50}$ nM |
| LHRH | 11 ± 1.6 | — | 82 ± 8 | — | 100 | 100 | 596 ± 40 | — | 1173 ± 146 | — | 100 | 100 | |
| [His$^5$Trp$^7$Gln$^8$]—LHRH | 5 ± 0.6 | <0.01 | 53 ± 8.6 | <0.05 | 46 | 65 | 404 ± 16 | 0.001 | 1161 ± 119 | NS | 67.8 | NS | 46:1 |
| [His$^5$Trp$^7$Leu$^8$]—LHRH | 2.5 ± 0.2 | <0.001 | 5 ± 0.25 | <0.001 | 23 | 6 | 369 ± 35 | 0.001 | 376 ± 69 | <0.001 | 62 | 32 | 12:1 |

| | Release 15 min. after sc injection | | | | | | | | | | | |
|---|---|---|---|---|---|---|---|---|---|---|---|---|
| | LH ng/ml | | | | LH % change | | FSH ng/ml | | | | FSH % change | |
| | Dosage of Peptide | | | | | | Dosage of Peptide | | | | | RRA |
| | 100 ng | P | 1000 ng | P | 100 ng | 1000 ng | 100 ng | P | 1000 ng | P | 100 ng | 1000 ng | ID$_{50}$ nM |
| LHRH | 24 ± 4 | — | 57 ± 7 | — | 100 | 100 | 465 ± 49 | — | 483 ± 84 | — | 100 | 100 | |
| [His$^5$Trp$^7$Gln$^8$]—LHRH | 17 ± 3 | NS | 66 ± 15 | NS | NS | NS | 403 ± 45 | NS | 486 ± 17 | NS | NS | NS | 46:1 |
| [His$^5$Trp$^7$Leu$^8$]—LHRH | 9 ± 1 | <.01 | 23 ± 3 | <.001 | 38 | 40 | 383 ± 48 | NS | 445 ± 33 | NS | NS | NS | 5:1 |

What is claimed:
1. p-Glu His Trp Ser His Gly Trp Gln Pro Gly-NH$_2$.
2. p-Glu His Trp Ser His Gly Trp Leu Pro Gly-NH$_2$.
3. p-Glu His Trp Ser His Gly Leu Arg Pro Gly-NH$_2$.
4. p-Glu His Trp Ser His Gly Trp Arg Pro Gly-NH$_2$.
5. p-Glu His Trp Ser Tyr Gly Leu Tyr Pro Gly-NH$_2$.
6. p-Glu His Trp Ser His Gly Leu Leu Pro Gly-NH$_2$.
7. p-Glu His Trp Ser His Gly Leu Tyr Pro Gly-NH$_2$.
8. p-Glu His Trp Ser His Gly Leu Gln Pro Gly-NH$_2$.
9. p-Glu His Trp Ser Tyr Gly Trp Tyr Pro Gly-NH$_2$.
10. p-Glu His Trp Ser Tyr Gly Trp Gln Pro Gly-NH$_2$.

* * * * *